United States Patent [19]
deMaria et al.

[11] Patent Number: 5,389,372
[45] Date of Patent: Feb. 14, 1995

[54] STABLE FORMULATION OF PLANT EXTRACT

[75] Inventors: Luigi deMaria; Claudio Lasciarrea; Pietro Micheli, all of Milan, Italy; Hein-Uwe Schmersahl, Limeshain, Germany

[73] Assignee: ASTA Medica Aktiengesellschaft, Dresden, Germany

[21] Appl. No.: 149,813

[22] Filed: Nov. 10, 1993

[30] Foreign Application Priority Data

Nov. 13, 1992 [GB] United Kingdom ............... 9223894

[51] Int. Cl.⁶ ............ A61K 9/16; A61K 35/78
[52] U.S. Cl. ............ 424/195.1; 424/493; 514/892
[58] Field of Search ............ 424/195.1, 493

[56] References Cited

U.S. PATENT DOCUMENTS

| | | | |
|---|---|---|---|
| 1,891,697 | 12/1932 | Tuvin | 424/195.1 |
| 1,891,698 | 12/1932 | Tuvin | 424/195.1 |
| 4,402,944 | 9/1983 | Callahan et al. | 424/180 |
| 4,476,121 | 10/1984 | Moss | 424/195 |
| 4,511,561 | 4/1985 | Madaus et al. | 424/195.1 |
| 5,173,296 | 12/1992 | Andre et al. | 424/195.1 |
| 5,232,699 | 8/1993 | Colliopoulos | 424/195.1 |

FOREIGN PATENT DOCUMENTS

| | | |
|---|---|---|
| M5549 | 4/1966 | France . |
| M6611 | 2/1969 | France . |
| 2646352 | 11/1990 | France . |
| 2412960 | 9/1975 | Germany . |
| 3837304 | 5/1990 | Germany . |
| 2067402 | 7/1981 | United Kingdom . |

OTHER PUBLICATIONS

Bezzegh et al CA. 102:77534j (1985) of Hung, HU 33032 29 Oct. 1984.
Dolder et al CA. 83: 197761s (1975).
Greve et al CA. 113: 218255k (1990) of Ger DE 3837304 10 May 1990.
Roberti CA. 71: 42291s (1969) of FR. M 5549 14 Apr. 1966.
Chicouri CA. 114: 129087k (1991) of FR 2646352 2 Nov. 1990.
Michaud CA. 74: 45601r 1971 of FR M, 6611 24 Feb. 1969.

*Primary Examiner*—Shep K. Rose
*Attorney, Agent, or Firm*—Cushman, Darby & Cushman

[57] ABSTRACT

A stable formulation of Sennosides with increased shelf-life and good solubility comprising a granulate containing Senna extract concentrate and, for each part by weight of Senna extract concentrate, 1 to 3 parts of weight of sucrose.

5 Claims, No Drawings

STABLE FORMULATION OF PLANT EXTRACT

The present invention relates to a stable form of Senna extract comprising a granulate containing Senna extract concentrate and, for each part by weight of Senna extract concentrate, 1 to 3 parts of weight of sucrose.

BACKGROUND OF THE INVENTION

Vegetables extracts based on compounds with phenolic or poliphenolic functional groups such as Sennosides are not stable in aqueous solutions in the presence of oxygen. The polymers which are formed cause turbidities and precipitations. This results in a loss of pharmaceutically active material.

In order to avoid these chemical instabilities, some pharmaceutical companies have put on the market pharmaceutical products containing Sennosides as the active substance in the solid form [Example: Pursennid (sugar coated tablets) from Sandoz or Agiolax (granulate) from Madaus (in Germany)] or in semisolid form [Example: Tamarine (jam) from Serono]. In the semisolid form (jam), the Sennosides are present in acid form and not as calcium salts. In the acid form Sennosides are not soluble in water and therefore are protected from the degradation process.

The degradation process of Sennosides in aqueous solution is slow and time-progressive; it increases with the increase of storage temperature. The degradation route of Sennosides involves a preliminary breakdown of glucosidic bonds and, soon thereafter, oxidation and polymerization of dianthrones or from hydrolysis.

On the basis of pharmacological research on senna extract, it has been confirmed that the specific influence on colon motility (laxative effect) of Sennosides must be ascribed to the anthrones or dianthrones and not to their degradation products (oxidized or polymerized products)

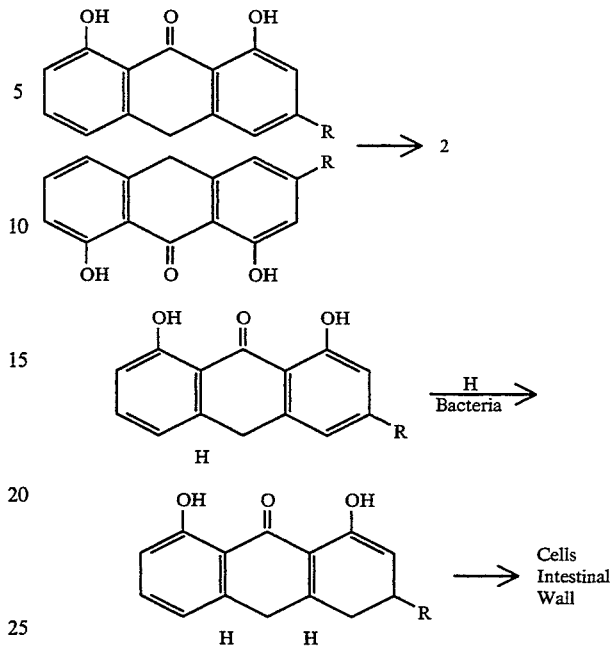

A reduction of pharmacological activity has to be expected when the degradation process increases.

The main disadvantage of the available formulations (actually on the market) is poor stability and therefore the short shelf-life period (18 months).

Stability data of the marketed solution (old form), in the form of a representative batch of X-Prep is given in Table 1. (Lot 220)

TABLE 1

| | Lot 220 | | | | |
| | | | Time | | |
| Controls | 0 | 6 months | 12 months | 18 months | 24 months |
| --- | --- | --- | --- | --- | --- |
| Characters | Brown syrup, sweet taste, chocolate smell | unmodified | unmodified | unmodified | unmodified |
| pH | 5.28 | 5.14 | 5.16 | 4.93 | 4.84 |
| Sennosides (Th: 2 mg/ml) | 2.149 mg/ml (107.45%) | 1.922 mg/ml (96.10%) | 1.858 mg/ml (92.90%) | 1.826 mg/ml (91.30%) | 1.773 mg/ml (88.65%) |

TABLE 2

| | Stability data on extemporary freshly prepared before analysis solution | | | | | | |
| | | | | Time | | | |
| Controls | 0 | 6 months | 12 months | 18 months | 24 months | 30 months | 36 months |
| --- | --- | --- | --- | --- | --- | --- | --- |
| Characters | Brown syrup, sweet taste, chocolate smell | comply | comply | comply | comply | comply | comply |
| pH | 5.06 | 5.18 | 5.10 | 5.15 | 5.38 | 5.27 | 5.31 |
| Sennosides (Th: 2 mg/ml) | 2.0092 mg/ml (100.46%) | 2.069 mg/ml (103.45%) | 2.048 mg/ml (102.40%) | 2.0508 mg/ml (102.54%) | 2.058 mg/ml (102.90%) | 2.035 mg/ml (101.75%) | 2.036 mg/ml ((101.18%) |

SUMMARY OF THE INVENTION

The object of the present invention is to provide a stable formulation of Sennosides with extended shelf life and better content of active principle. A further object is to provide such a formulation which has good taste and which is easy to use. These objects are achieved in a granulate containing Senna extract concentrate and, for each part by weight of Senna extract concentrate, 1 to 3 parts of weight of sucrose

Stability Data on New Formulation

The stability data of the now available composition of the present invention, based on X-Prep, are given in Table 2.

From data obtained in stability studies it has been found that the active principle (Sinusoids) in the granulate are stable for at least 3 years. This is significantly more than the stability of the forms according to the state of the art. Satisfactory stability of Sennosides in the extemporary prepared solution for at least 3 months (suggested shelf-life period) have been found at room temperature (II climatic zone) storage conditions and for at least 6 months for solution stored in refrigerator. The climatic zones are defined according to "Pharmazeutische Technologie", Ed. Sucker, Fuchs, Speiser, Thieme, 1991, page 704. In this shelf-life of extemporary prepared solution we can propose a narrower variation of content of active substance: ±5% instead of ±10% (actual range, for 18 months storage, of ready-to-use X-Prep syrup).

Experimental Data on the Speed of Solution for New Formulation

The first step examined in galenic trials for extemporary solution realization was the solution speed of the powder containing Sennosides into the solution with excipients. In preliminary galenic trials, it was decided to replace the raw material Senna dried extract with 5% of Sennosides with a raw material with higher content of Sennosides (Senna extract with 45% of Sennosides supplied by INDENA S.p.A.) for the following reasons.

1) the quantity of raw material to be employed is too high (technical problem for vessel size),
2) shaking time: >5' with vigorous shaking and with residual lumps (incomplete solution).

The following data gives the result of experiments with Senna extract (45% of Sennosides) and excipients solution containing 66% of sucrose:

Results: a) shaking time too long: 3'-5' with vigorous shaking
b) incomplete solution of the powder with small lumps formation
c) after some storage period (6 months to 1 year) because of the hygroscopicity, the powder appeared a little sticky and some difficulties had been found for powder falling from vessel into solution (after the break of the bottom of vessel).

This means that the initial dryness of the powder does not solve the problem.

In accordance with the present invention, it has been found, that a stable, free-flowing and readily soluble granulate of senna glycosides may be obtained by increasing the sucrose content up to the ratio of 1: 2 (weight ratio) with respect to dried senna extract.

The following data shows the results obtained using Senna granulate (1:2) with sucrose and excipients solution with of sucrose Results: a) shaking time for complete solution: 1'-2' with vigorous shaking
b) solution of the powder after shaking: almost complete
c) flowability of granulate: practically unmodified after storage period of 3 years Further it has been found, that a reduction of shaking time can be achieved by reducing the sucrose content in the excipient solution to 40% (weight %) of sucrose.

The following data shows the result of using of Senna granulate (1:2) with sucrose and excipients solution with 40% of sucrose:

Results: a) shaking time for granulate solution: <1' with moderate shaking
b) solution of the powder (granulate) after shaking: complete
c) flowability of granulate: practically unmodified after storage period of 3 years These data show clearly, that the problem of reducing the content of active principle, increased stability and increased shelf-live, easy and complete solubility can be achieved by the formulation, a granulate, containing a dried senna extract with sucrose and an excipient solution with sucrose.

This makes it possible to place the granulate in a chambered stopper, according to the German Patent 22 40 030 or German Patent 23 63 054.

DETAILED DESCRIPTION OF PREFERRED EMBODIMENTS

EXAMPLE 1

| X-Prep New Formulation for Extemporary solution | | |
|---|---|---|
| A) Granulate | | |
| 1 g contains | | |
| Senna extract concentrate | g | 0,334 |
| (equivalent to Sennosides A + B) | (g | 0,15) |
| Sucrose | g | 0,666 |
| | g | 1,000 |
| B) Excipients Solution | | |
| 100 ml of excipients solution contain | | |
| Sucrose | g | 40 |
| Ethyl alcohol | ml | 7,36 |
| Chocolate flavor V 8127 | ml | 0,375 |
| Cocoa flavor 59297 A | ml | 0,0025 |
| Propyl Paraben | g | 0,02 |
| Methyl Paraben | g | 0,2 |
| Purified water q.s. ad | ml | 100 |

The presentation form consists of:

Plastic vessel with g 1,0 of granulate

Glass ambered bottle containing ml 75,0 of excipients solution.

Primary package: breaker assembled with plastic vessel set in to the mouth of the bottle; closure with plastic, child-proof, screw cap.

What is claimed is:

1. A granulate consisting essentially of Senna extract concentrate and, for each part by weight of Senna extract concentrate, 1 to 3 parts of weight of sucrose.

2. A package comprising a chambered stopper containing a granulate according to claim 1 and a bottle with a liquid.

3. A package according to claim 2 in which the liquid is a solution of 30 to 60 weight % sucrose in water.

4. A method of treating diseases which respond to Senna extract which comprises administering an effective amount of the granulate set forth in claim 1.

5. A combination consisting essentially of (a) a granulate consisting of Senna extract concentrate and, for each part by weight of Senna extract concentrate, 1 to 3 parts of weight of sucrose and (b) a solution of 30 to 60 weight % sucrose in water.

* * * * *